(12) United States Patent
Shimko et al.

(10) Patent No.: US 9,283,013 B2
(45) Date of Patent: Mar. 15, 2016

(54) FILLING SYSTEMS FOR BONE DELIVERY DEVICES

(71) Applicant: Warsaw Orthopedic, Inc., Warsaw, IN (US)

(72) Inventors: Daniel A. Shimko, Germantown, TN (US); Kerem N. Kalpakci, Memphis, TN (US); Jason A. Rister, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 315 days.

(21) Appl. No.: 13/829,416

(22) Filed: Mar. 14, 2013

(65) Prior Publication Data

US 2014/0261855 A1 Sep. 18, 2014

(51) Int. Cl.
*A61B 17/88* (2006.01)
*A61F 2/28* (2006.01)
*A61F 2/46* (2006.01)
*A61F 2/30* (2006.01)
*A61F 2/44* (2006.01)

(52) U.S. Cl.
CPC .............. *A61B 17/8802* (2013.01); *A61F 2/28* (2013.01); *A61F 2/4601* (2013.01); *A61F 2002/2835* (2013.01); *A61F 2002/30062* (2013.01); *A61F 2002/30588* (2013.01); *A61F 2002/30784* (2013.01); *A61F 2002/4495* (2013.01)

(58) Field of Classification Search
CPC . A61F 2/28; A61F 2/4601; A61F 2002/2835; A61F 2002/30062; A61F 2002/30588; A61F 2002/30784; A61F 2002/4495; A61B 17/8802; A61B 17/8805; A61B 2017/8813; A61B 17/8816; A61B 17/8819; A61B 17/8822; A61B 17/8825; A61B 17/8833; A61B 2017/8838

USPC .................. 141/2, 27, 108, 109; 606/92–94
See application file for complete search history.

(56) References Cited

U.S. PATENT DOCUMENTS

| | | | | |
|---|---|---|---|---|
| 2,508,699 | A | * | 5/1950 | Welsh ........................... 141/108 |
| 2,603,093 | A | * | 7/1952 | Cordova ......................... 73/427 |
| 2,698,996 | A | * | 1/1955 | Hickerson ....................... 30/123 |
| 3,490,501 | A | * | 1/1970 | Lefebvre et al. ................ 141/84 |
| 3,727,802 | A | * | 4/1973 | Schnurmacher .............. 222/205 |
| 4,646,795 | A |   | 3/1987 | Hebron et al. |
| 5,092,491 | A | * | 3/1992 | Matz ............................. 222/135 |
| 5,202,021 | A |   | 4/1993 | Griffin et al. |
| 5,353,531 | A |   | 10/1994 | Doucette |
| 5,377,879 | A | * | 1/1995 | Isaacs ........................... 222/205 |
| 5,580,111 | A | * | 12/1996 | Bohn ............................. 294/1.3 |
| 5,586,821 | A | * | 12/1996 | Bonitati et al. ............... 366/139 |
| D387,514 | S | * | 12/1997 | Savicki ........................ D30/162 |

(Continued)

*Primary Examiner* — Timothy L Maust
(74) *Attorney, Agent, or Firm* — Sorell Lenna & Schmidt LLP

(57) ABSTRACT

A filling system for delivery of at least one substance to a covering is provided. The filling system comprises at least a funnel shaped container and a plunger. The funnel shaped container includes a scoop portion connected to a hollow barrel. The barrel is configured for insertion into the covering, the plunger adapted for pushing the at least one substance down the hollow barrel into the covering. The filling system can also include a spatula. A kit including a funnel shaped container, a plunger adapted to push a substance down the barrel of the funnel shaped container, a spatula, a retainer for keeping the kit elements in place and trays for protecting them from the environment are also provided. A method of use utilizing the filling system is also provided.

19 Claims, 7 Drawing Sheets

(56) References Cited

U.S. PATENT DOCUMENTS

| | | | |
|---|---|---|---|
| 5,716,087 A | 2/1998 | Backich et al. | |
| 5,738,399 A | 4/1998 | Mitchell | |
| 5,951,160 A * | 9/1999 | Ronk | 366/130 |
| 6,019,765 A * | 2/2000 | Thornhill et al. | 606/94 |
| 6,294,187 B1 | 9/2001 | Boyce et al. | |
| 6,440,444 B2 | 8/2002 | Boyce et al. | |
| 6,478,825 B1 | 11/2002 | Winterbottom et al. | |
| 6,696,073 B2 | 2/2004 | Boyce et al. | |
| 6,723,131 B2 | 4/2004 | Muschler | |
| 7,083,648 B2 | 8/2006 | Yu et al. | |
| 7,097,027 B1 | 8/2006 | Chen | |
| 7,191,553 B2 | 3/2007 | Doucette et al. | |
| 7,306,611 B2 * | 12/2007 | Cirotteau et al. | 606/92 |
| 7,387,507 B2 | 6/2008 | Schuler | |
| 8,042,688 B2 | 10/2011 | Parks et al. | |
| 8,100,452 B1 | 1/2012 | Homewood | |
| 8,246,572 B2 * | 8/2012 | Cantor et al. | 604/60 |
| 8,303,599 B2 * | 11/2012 | Hess et al. | 606/92 |
| 8,486,080 B2 * | 7/2013 | McKay | 606/94 |
| 8,673,021 B2 * | 3/2014 | Orr et al. | 623/23.72 |
| 2005/0241965 A1 * | 11/2005 | Kurc | 206/219 |
| 2005/0251267 A1 | 11/2005 | Winterbottom et al. | |
| 2005/0283255 A1 | 12/2005 | Geremakis et al. | |
| 2006/0052879 A1 | 3/2006 | Kolb et al. | |
| 2006/0216323 A1 | 9/2006 | Knaack et al. | |
| 2007/0088443 A1 | 4/2007 | Hanssen et al. | |
| 2007/0098756 A1 | 5/2007 | Behnam | |
| 2007/0110820 A1 | 5/2007 | Behnam | |
| 2007/0170732 A1 * | 7/2007 | Platt | 294/1.3 |
| 2007/0191963 A1 | 8/2007 | Winterbottom et al. | |
| 2009/0130173 A1 | 5/2009 | Behnam et al. | |
| 2009/0192474 A1 | 7/2009 | Wei et al. | |
| 2009/0234277 A1 | 9/2009 | Wei et al. | |
| 2009/0240255 A1 | 9/2009 | McKay et al. | |
| 2010/0203155 A1 | 8/2010 | Wei et al. | |
| 2010/0249720 A1 * | 9/2010 | Biyani et al. | 604/218 |
| 2011/0015640 A1 * | 1/2011 | Hess et al. | 606/93 |
| 2011/0054408 A1 | 3/2011 | Wei et al. | |
| 2011/0071536 A1 | 3/2011 | Kleiner et al. | |
| 2011/0152754 A1 | 6/2011 | Cantor et al. | |
| 2012/0097556 A1 | 4/2012 | Gascoine | |
| 2012/0297902 A1 | 11/2012 | Leventhal et al. | |

* cited by examiner

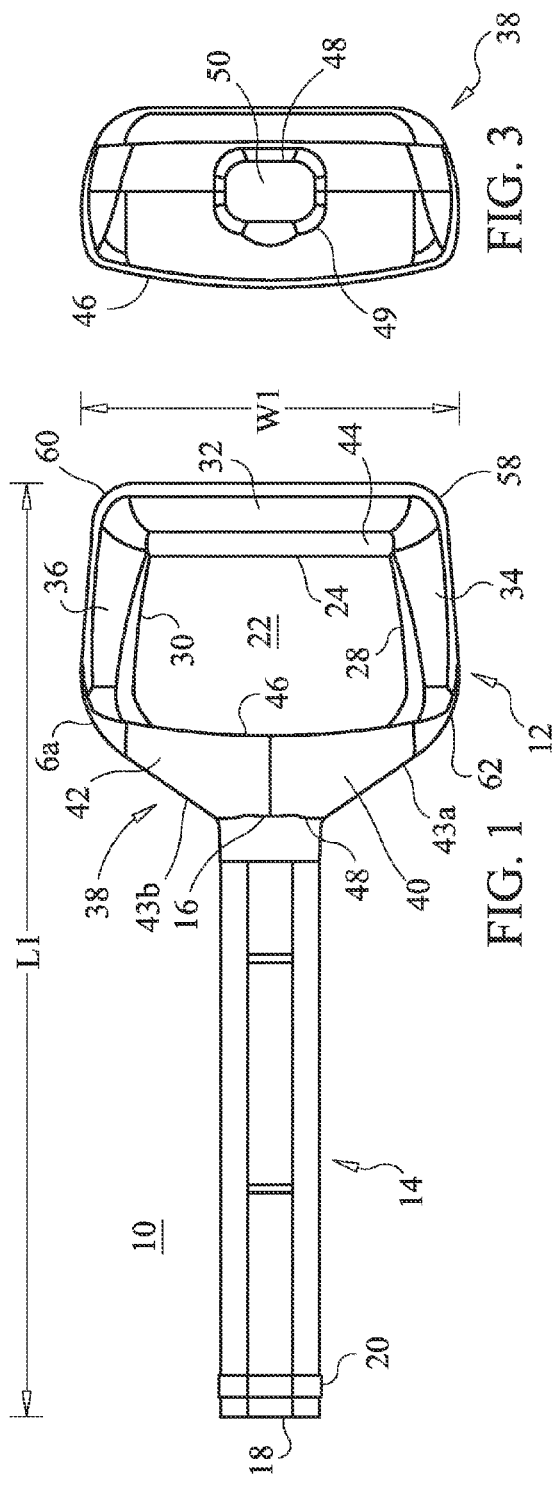
FIG. 1
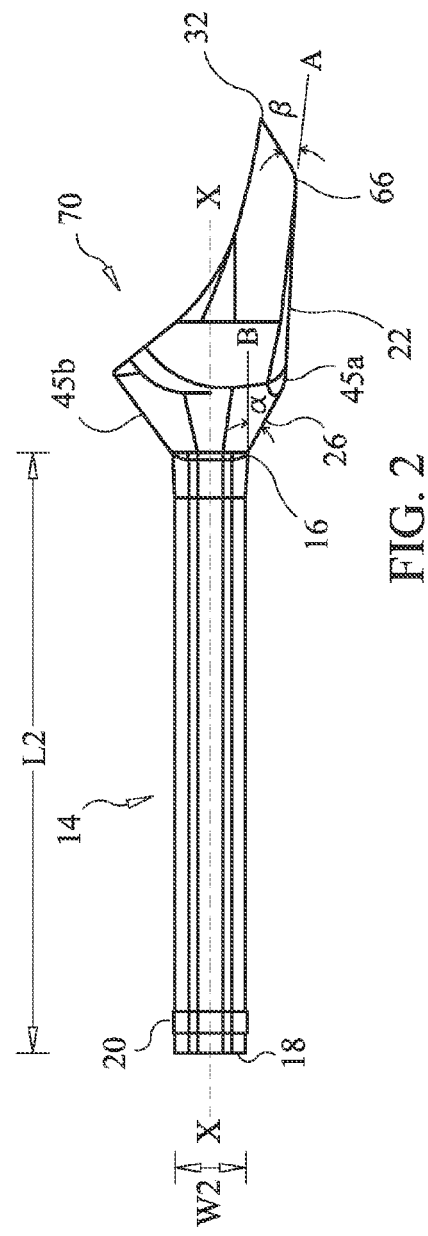
FIG. 2
FIG. 3

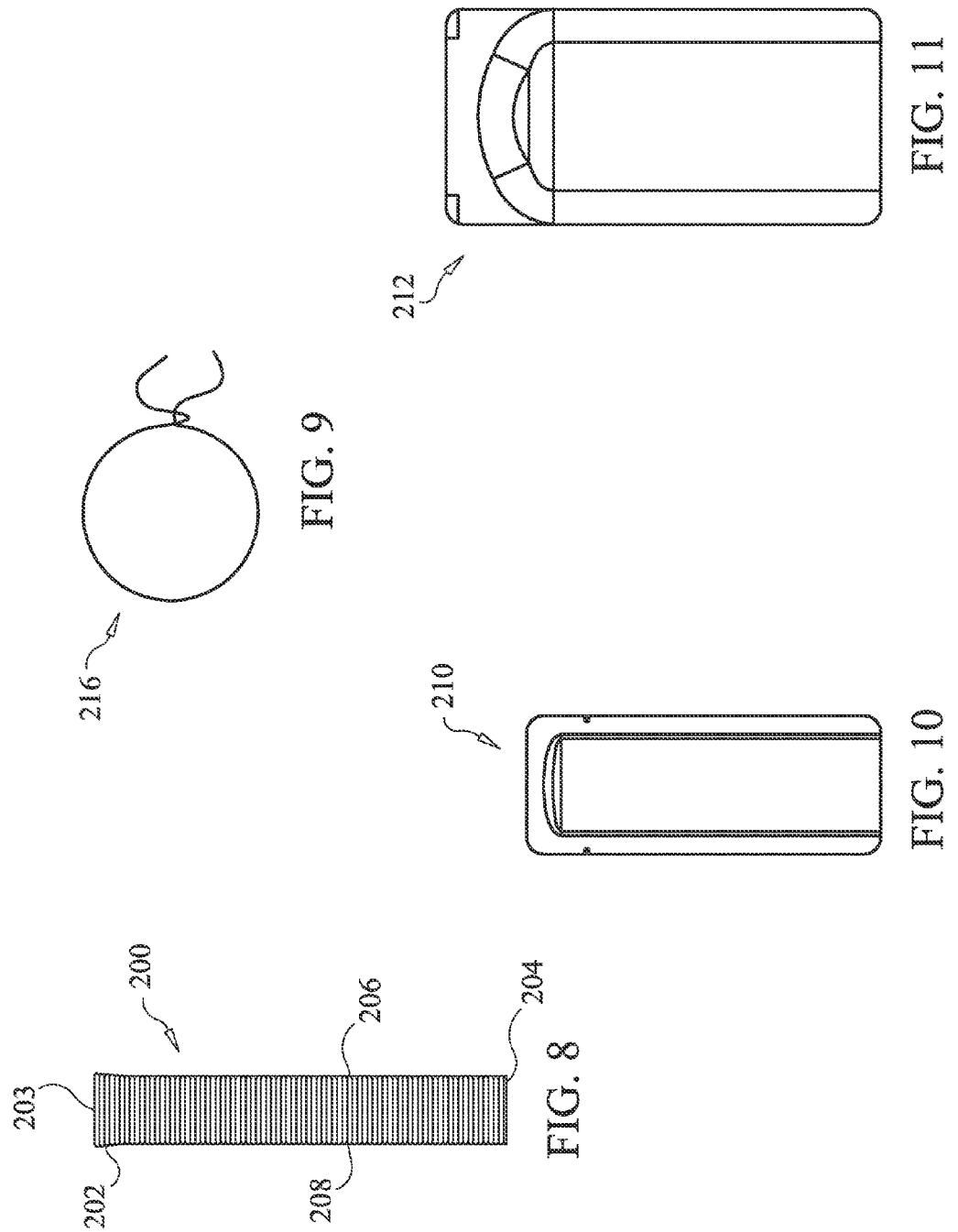

FILLING SYSTEMS FOR BONE DELIVERY DEVICES

FIELD

Filling systems for delivering a substance or material to a bone delivery device at a surgical site are provided. More particularly, filling systems comprising a funnel shaped container and a plunger for adding material to a covering are provided.

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damaged cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible. Generally, the formed implant, whether monolithic or particulated and in a carrier, is substantially solid at the time of implantation and thus does not conform to the implant site. Further, the implant is substantially complete at the time of implantation and thus provides little ability for customization, for example by the addition of autograft.

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Demineralized bone matrix ("DBM") implants have been reported to be particularly useful. Demineralized bone matrix is typically derived from cadavers. The bone is removed aseptically and/or treated to kill any infectious agents. The bone is then particulated by milling or grinding and then the mineral components are extracted for example, by soaking the bone in an acidic solution.

Current DBM formulations have various drawbacks. First, while the collagen-based matrix of DBM is relatively stable, the active factors within the DBM matrix are rapidly degraded. The osteogenic activity of the DBM may be significantly degraded within 24 hours after implantation, and in some instances the osteogenic activity may be inactivated within 6 hours. Therefore, the factors associated with the DBM are only available to recruit cells to the site of injury for a short time after transplantation. For much of the healing process, which may take weeks to months, the implanted material may provide little or no assistance in recruiting cells.

Attempts to overcome these problems have lead researchers to utilize delivery systems such as enclosed polymer mesh bags to release DBM at a surgical site. However, any additional bone graft material, such as autologous bone or growth factors, would have to be placed underneath or on top of the DBM mesh bag which approach does not always induce new bone formation.

Thus, there is a need to improve the efficacy and consistency of DBM delivery systems by mixing the DBM particles/fibers with other bone graft materials such as autologous bone and other bioactive agents throughout the bag by providing expeditious and simple devices of filling the bag prior to or during the surgical procedure. It would therefore be desirable to provide filling systems for bone graft material delivery devices which address this need.

SUMMARY

A filling system for delivery of at least one substance to a covering is provided. The filling system comprises at least a funnel shaped container and a plunger. The funnel shaped container includes a scoop portion connected to a hollow barrel. The scoop portion includes a flat base connected to a front wall, side walls and a funnel shaped neck leading to an opening of the hollow barrel. The barrel has a top end and a bottom end, the top end being connected to the funnel shaped neck of the funnel shaped container. At its bottom end, the barrel contains a bulge configured for easy insertion into the covering. The plunger contains an elongated portion connected to a flared handle, wherein the elongated portion of the plunger extends for substantially the length of the barrel and adapted to push the at least one substance down the hollow barrel into the covering. At one end the plunger includes a wider portion having a diameter larger than that of the elongated portion adapted for stopping the advancement of the elongated portion into the hollow rod of the barrel.

In some embodiments, the filling system also contains spatula for dispensing the at least one substance into the funnel shaped container. The spatula contains a stalk portion having two ends, a conical tip at one end and a shovel area at the opposite end.

In various embodiments, the filling system described in this application is utilized to fill a delivery device, such as a biodegradable covering configured for implantation into a bone defect site is provided. The covering may include a single or multi-compartment structure. In various embodiments, the covering includes at least one compartment defining an opening for loading the at least one compartment with at least one substance.

In various embodiments, the closing member of the covering includes drawing strings, stitches, sutures, heat seals, adhesive seals, pressure fittings or combinations thereof.

In some embodiments, the drawstring can be slidably received in a casing extending about the periphery of the opening of the at least one compartment and have two apertures positioned proximate each other so that when the end portions of the drawstring are pulled out of the drawstring casing through the two apertures, the periphery of at least one compartment gathers to reduce the opening of the at least one compartment in size sufficiently to enclose the at least one substance therein. The at least one substance comprises autograft, allograft, demineralized bone matrix fibers and demineralized bone matrix chips in a 30:60 ratio or a combination thereof.

In various embodiments, the present application also provides a kit to facilitate the placement of at least one substance within a covering. The kit described herein comprises a funnel shaped container having a scoop portion connected to a barrel and a plunger, the plunger adapted to slide through the barrel of the funnel shaped container for pushing the at least one substance into the covering. The kit also contains an inner tray with recesses configured to receive the funnel and the plunger. The kit also includes a retainer positioned on top of the inner tray, the retainer for holding the funnel shaped container and plunger in place; an inner lid and an outer lid for sealing the funnel shaped container and the plunger from the environment are also contained in the kit of this application. In some embodiments, the kit can further include a spatula, the spatula having a stalk portion and a truncated shovel end, the shovel adapted to pack the at least one substance into the funnel shaped container.

In various embodiments, a method is provided for filling a covering with the at least one substance, the method comprising providing a covering having at least one flared opening; providing a funnel shaped container having a scoop portion connected to a hollow barrel, the barrel configured for insertion into the flared opening of the cover; providing at least one substance into the funnel shaped container; providing a plunger having an elongated portion and a flared handle, and pushing the at least one substance with the plunger through the barrel into the covering.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION OF THE DRAWINGS

FIG. 1 depicts a perspective top view of a funnel shaped container according to an aspect of the present application;

FIG. 2 depicts a side view of a funnel shaped container according to another aspect of the present application;

FIG. 3 depicts a top detail view of the neck portion of a funnel shaped container according to another aspect of the present application;

FIG. 8 depicts a side view of a mesh bag according to an embodiment of the present application;

FIG. 9 depicts a detail of suture ties of mesh bag illustrated in FIG. 8;

FIG. 10 depicts a top view of an inner foil tear pouch according to an embodiment of the present application;

FIG. 11 depicts a top view of an outer foil peel pouch according to another embodiment of the present application;

Figure 4:
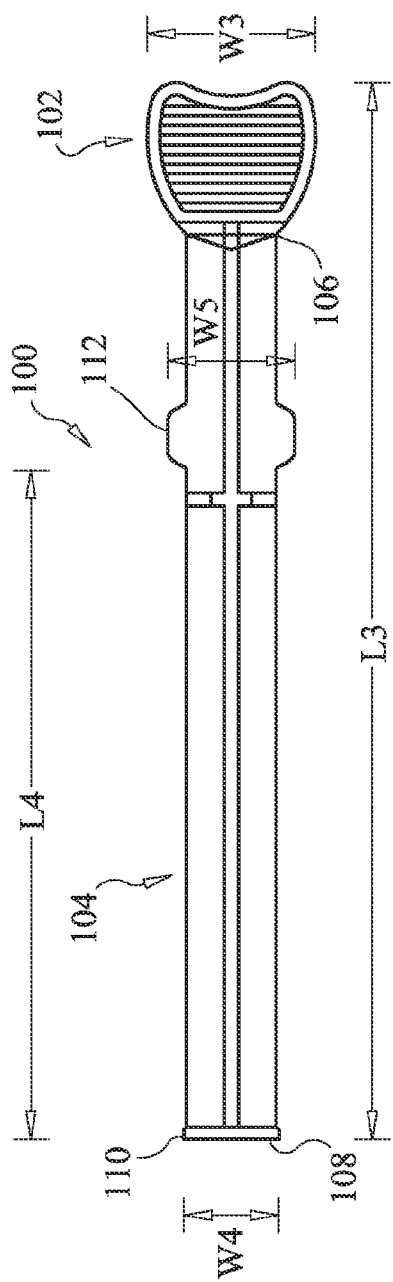
FIG. 4 depicts a cross-sectional view of a plunger according to an aspect of the present application.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

It is noted that, as used in this specification and the appended claims, the singular forms "a," "an," and "the," include plural referents unless expressly and unequivocally limited to one referent. For example, reference to "a covering" includes one, two, three or more coverings.

Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

Biocompatible, as used herein, refers to materials that, upon administration in vivo, do not induce undesirable long-term effects.

Bone, as used herein, refers to bone that is cortical, cancellous or cortico-cancellous of autogenous, allogic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the application. In some embodiments, demineralized bone has less than 95% of its original mineral content. Demineralized is intended to encompass such expressions as "substantially demineralized," "partially demineralized," and "fully demineralized."

Demineralized bone matrix, as used herein, refers to any material generated by removing mineral material from bone tissue. In preferred embodiments, the DBM compositions as used herein include preparations containing less than 5% calcium and preferably less than 1% calcium by weight.

Partially demineralized bone (e.g., preparations with greater than 5% calcium by weight but containing less than 100% of the original starting amount of calcium) are also considered within the scope of the application.

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoimplant, as used herein, refers to any bone-derived implant prepared in accordance with the embodiments of this application and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The terms "upper", "lower", "top", "bottom", "side", "proximal", "distal" and so forth have been used herein merely for convenience to describe the present invention and its parts as oriented in the drawings. It is to be understood, however, that these terms are in no way limiting to the disclosure since the delivery systems described herein may obviously be disposed in different orientations when in use.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Introduction

A filling system for delivery of at least one substance or material to a covering at a surgical site is provided. In various embodiments, the filling system comprises a funnel shaped container and a plunger. The funnel shaped container comprises a scoop portion connected to a hollow barrel, wherein the barrel is configured for insertion into a covering. The plunger is adapted for slidingly pushing the at least one substance down the hollow barrel into the covering system. A spatula can be used to dispense a desired amount of material into the covering. The covering can be a mesh bag having at least one compartment configured to receive at least one substance, for example, autograft chips for delivery to a surgical site.

Funnel Shaped Device

FIGS. 1, 2 and 3 illustrate a funnel shaped container 10 comprising a scoop portion 12 and barrel portion 14. Scoop portion 12 comprises a flat base 22 connected to a front wall 32, opposite side walls 34 and 36, and a funnel shaped neck or rear portion 38. In some aspects, flat base 22 is substantially rectangular and is defined by front edge 24, rear edge 26 (not shown) and side edges 28 and 30. Front wall 32 is vertical and extends upwardly and slightly inwardly from flat base 22. Front wall 32 forms an acute angle β between bottom edge 66 of wall 32 and plane A tangential to flat base 22 as illustrated in FIG. 2. In various aspects, angle β can range between 10° and 60°, in a range between 10° and 45°. In some embodiments, a substantially rectangular lower front portion 44 transitions from flat base 22 to front wall 32. Opposite side walls 34 and 36 are substantially vertical and extend upwardly and slightly inwardly from flat base 22. Side wall 34 tapers upwardly from first front end 58 to first rear end 62. Side wall 36 tapers upwardly from second front end 60 to second rear end 64.

Rear portion or neck 38 of scoop portion 12 comprises a first and second fluted portions 40 and 42 which are contiguous to each other and form a top rim 46 and a bottom edge 48 defining an opening 50 configured to join and open into front end 16 of barrel 14. First and second fluted portions 40 and 42 join side walls 34 and 36 at first rear end 62 and second rear end 64, respectively. First and second fluted portions 40 and 42 comprise front portions 43a and 43b and rear portions 45a and 45b as shown in FIGS. 1 and 2, respectively. Rear portions 45a and 45b, each separately form angle α with a horizontal plane B parallel to the longitudinal axis X-X of funnel shaped container 10. Angle α can range between 10° and 90°, in a range between 10° and 60°, or in a range between 10° and 45°. Fluted portions 40 and 42 also join flat base 22 at rear edge 26 as shown in FIG. 2. First and second fluted portions 40 and 42 together with side walls 34 and 36 and front wall 32 define an axial access channel 70. Axial access channel 70 is substantially funnel shaped in the area defined by fluted portions 40 and 42. All side walls around access channel 70 have rounded ends and they may be formed of one continuous curved sheet having no flat areas or may be segmented by a plurality of curved or planar segments welded together along their adjacent seams so as to form one contiguous slightly curved enclosure defining access channel 70. In various embodiments, as illustrated in FIG. 1, the length L1 of funnel shaped container is about 219.3 mm and the width W1 is about 88.7 mm.

With further reference to FIGS. 1 and 2, barrel 14 includes a hollow tube or cylinder having a front end 16 and rear end 18. At rear end 18, barrel 14 contains a bulge 20 configured to be easily insertable into a covering device, for example a polymer bag 200 (not shown). In some embodiments, after insertion, bulge 20 can be used to attach polymer bag 200 upon it and or tie it with suture ties 216 shown in FIG. 9 around bulge 20 in order to receive bone graft material quickly and in controlled manner. In certain embodiments, barrel 14 can have a length L2 of about 141 mm and a width W2 of about 16.5 mm.

Funnel shaped container 10 can be fabricated by injection molding of plastic material comprising rigid, surgical grade plastic or metal material.

FIG. 3 depicts a top view of neck 38 illustrating opening 50 leading into barrel 14. In certain embodiments, opening 50 is defined by an approximately rectangular flange 49 formed at the bottom edge 48 of neck 38 providing a secure welded joint to barrel 14. In some embodiments, the width of opening 50 is about 14 mm and the length is about 21 mm.

Plunger

Figure 5:
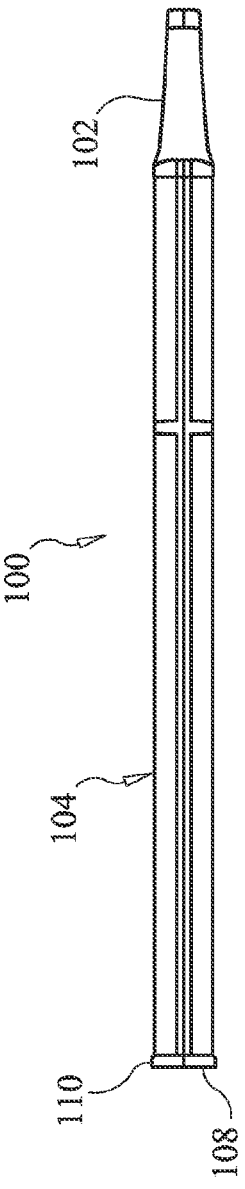
FIG. 5 depicts a side view of a plunger shown in FIG. 4 according to an aspect of the present application.
Figure 6:
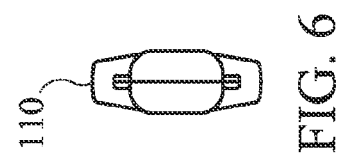
FIG. 6 depicts a top view of a rib of the plunger illustrated in FIG. 4 according to an aspect of the present application.

Referring now to FIGS. 4, 5 and 6, a plunger 100 is shown for use with funnel shaped container 10 to place bone graft into a bone bag or pouch 200. Plunger 100 has generally the same geometry as the hollow portion or barrel 14 of the funnel shaped container 10. Plunger 100 comprises an elongated portion 104, in some embodiments, extending at least the same length as barrel 14 from a top end 106 to a bottom end 108. Plunger 100 further comprises a flared handle 102 connected to elongated portion 104 and configured for easy holding and manipulation of plunger 100. The flared handle also stops the plunger from advancing too far within the barrel. At top end 106 and before joining flared handle 102, elongated portion 104 further comprises a projection or bulge 112, which is a wider region having a diameter larger than that of elongated portion 104. Projection or bulge 112 functions to stop the advancements of elongated portion 104 into barrel 14. At bottom end 108, elongated portion 104 further comprises a bottom rib 110, which functions to create a seal between barrel 14 and plunger 100.

FIG. 5 is a side view of plunger 100 illustrated in FIG. 4. FIG. 6 is a top view of bottom rib 110. With further reference to FIGS. 4 and 6 in some aspects, the plunger can have a length L3 of about 229 mm and a width W3 at the flared handle 102 of about 106 mm. In certain aspects, the length L4 of elongated portion 104 up to projection 112 can be about 146 mm and the width W4 of rib 110 can be about 20.5 mm. In other aspects, width W5 of the wider region or projection 112 is about 27.5 mm.

Spatula

Figure 7:
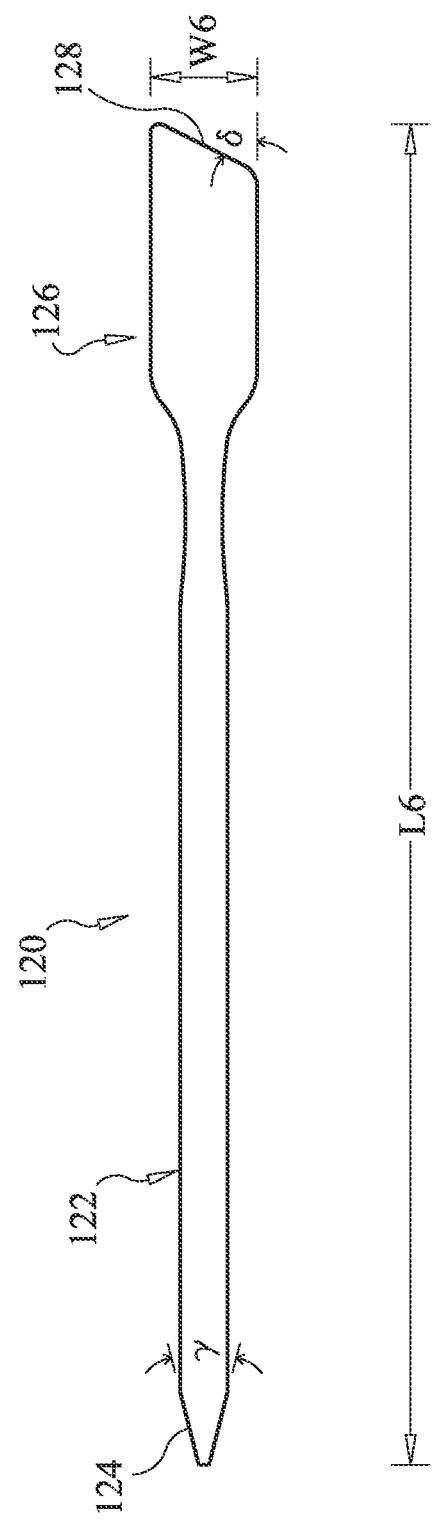
FIG. 7 depicts a side view of a spatula according to an aspect of the present application.

FIG. 7 illustrated a spatula 120 used to dispense or collect a small quantity of bone graft material for introduction into funnel shaped container 10. Spatula 120 includes a stalk portion 122 having a conical tip 124 at one end and a truncated shovel area 126 at the opposite end. Depending on the application, either end can be used for holding material and manipulating amounts of bone graft into funnel device 10. Conversely, either end can be used for holding the spatula. In one embodiment, tip 124 forms an acute angle γ of about 28°. The truncated shovel area 126 of spatula 120 forms an angle δ of about 63° with the horizontal and its truncated end 128. In some embodiments, spatula 120 has a length L6 of about 181 mm and a width W6 at the truncated shovel end of about 14 mm.

Covering, Holding and Filling Devices

FIG. 8 illustrates a bone delivery device system having a covering 200. Covering 200 comprises a top end 202, a bottom end 204, side walls 206 and 208. At top end 202, covering 200 is flared to facilitate insertion of rear end 18 of barrel 14. In the illustrated covering 200, a cylindrical configuration is provided. Covering 200 comprises a length, width and cross section which may vary depending on the application for the covering. The cross section can be tubular or cylindrical, and in alternative embodiments, any cross-sectional shape, such as a generally circular, oval, rectangular, generally square, generally star, or any other suitable shape may be used. In the embodiment shown in FIG. 8, the covering 200 comprises a mesh material and can be a mesh bag. Within these coverings or mesh bags, there can be provided a particulated substance such as milled bone or DBM particles/fibers, wherein the ratio of DBM fibers to DBM chips is about 30:60.

In certain embodiments, the length L7 of the overall covering body 200 will range from about 1 cm to about 15 cm, the width W7 will range from about 1 cm to about 20 cm, and the thickness T will range from about 0.5 cm to about 9 cm. Length L7 may range from about 2.5 to about 8 cm, width W7 may range from about 2.5 to about 8 cm, and thickness T may range from about 1 to about 10 cm.

As to volume, advantageous implant bodies 100 can have a total volume of at least about 2 cubic centimeters (cc), e.g. in the range of about 2 cc to about 100 cc, and more typically in the range of about 10 cc to about 50 cc, although both smaller and larger overall volumes may also be used.

In various embodiments, top end 202 of covering 200 defines an opening 203 and closing member, such as suture ties or drawstrings 216, illustrated in FIG. 9. In various embodiments, the suture ties are proximately located to opening 203. Covering 200 can be packaged in an inner foil tear pouch 210 and an outer foil peel pouch 212 as illustrated in FIGS. 10 and 11, respectively.

In various other embodiments, the suture ties or drawstrings 216 used to close the opening of the covering can be wires made of nitinol or any other shape memory alloy. For example, nitinol wires can be slidably received in the casing around the perimeter of the opening of the cover and upon the removal of the funnel, the nitinol wires would relapse to a closed position thereby securing the allograft chips or other graft material inside the covering.

Generally, the covering may be a single or multi-compartment structure capable of at least partially retaining a substance provided therein until the covering is placed at a surgical site as more particularly described in United States published application No. 20100203155 incorporated herein by reference as if set forth in full. In some embodiments, the covering may be substantially non-expandable or minimally deformable. In some embodiments, the covering may be a temporary covering wherein the covering is substantially resorbable. For example, in some embodiments, the covering may be formed of a material that is substantially resorbed within 2 weeks, within 4 weeks, within 12 weeks, or within other suitable time frame. Accordingly, in some embodiments, a delivery system including the covering may be a temporary delivery system. The covering may include one or more attachment mechanisms for retaining the covering at the surgical site. The attachment mechanism may be a mechanical attachment mechanism, a physical attachment mechanism, a biological attachment mechanism or a chemical attachment mechanism, or may employ combinations of these. The attachment mechanism may be used to attach the covering to skeletal or soft tissue proximate the surgical site.

In some embodiments, the covering may be used for containment of particulate or morselized materials (the substance provided in the covering), optionally to provide a focus or concentration of biological activity. In some embodiments, the covering may be used for containment of a substance one or more of bone particles, bone fibers, other osteoinductive or osteoconductive materials, BMP, antibiotics, or other materials.

In some embodiments, the covering may be used for maintaining materials (the substance provided in the covering) in spatial proximity to one another, possibly to provide a synergistic effect. In some embodiments, the covering may be used to control availability of a substances provided within the covering to cells and tissues of a surgical site over time. In some embodiments, the covering may be used for delivery through a limited opening, such as in minimally invasive surgery or mini-open access. In some embodiments, the covering may be used to deliver morselized or particulated materials (the substance provided in the covering) in pre-measured amounts. In other embodiments, the substance may be liquid or flowable, or combinations of these with particulate, morselized, and/or other materials.

In various embodiments, the covering may contain a substance or material such as a graft material. The covering limits, and in some embodiments eliminates, graft migration and maintains graft density. The delivery system, with contained substance or material, may be configured to conform to surrounding bony contours or implant space. In some embodiments, the delivery system provides a pathway for healing/cell penetration and tissue ingrowth. Thus, the covering may facilitate transfer or diffusion of materials into and out of the covering. For example, the covering may facilitate diffusion from the covering of a substance provided within the covering or may facilitate diffusion into the covering of materials in the surgical site, such as cells and tissues, into the covering. The covering may be configured to permit diffusion of some materials while substantially preventing diffusion of other materials. Further, in various embodiments, the covering may be configured such that diffusion is permitted into or out of certain portions of the covering but not other portions of the covering. In some embodiments, the covering may merely retain a substance at the surgical site.

Covering Material

The covering may comprise a structural material and, in some embodiments, a functional material. The structural material may comprise a mesh material, a polymeric material, or other. The functional material may comprise, for example, a radiopaque material, a bacteriocidal material, or other material.

In various embodiments, in accordance with the specific application for which the covering is being used, the covering may be rigid, may be flexible, may be non-elastic, or may be elastic. The covering material may be braided, woven, nonwoven shape memory, particulate, threaded, porous, or nonporous. In some embodiments, the covering comprises a pouch with demineralized bone material disposed in the pouch uniformly or in discrete positions within the pouch.

The covering may participate in, control, or otherwise adjust the release of the substance. For example, the covering may act as a selectively permeable membrane and/or may be porous, with the level of porosity being related to the nature of the substances inside the covering. Thus, the material for and configuration of the covering may be selected or adjusted based on desired release characteristics. Specific properties that may be adjusted include thickness, permeability, porosity, strength, flexibility, elasticity, and others of the covering material. It is to be appreciated that some of these properties may depend on others. For example, the thickness and porosity of the material may contribute to its strength, flexibility, and elasticity.

In some embodiments, the covering may be porous to fluid and/or cells, may be biocompatible, and may be resistant to rupture (including should the substance provided therein swell). In some embodiments, the covering with the substance provided therein may be loadbearing. The covering may be resorbable or non-resorbable. The covering may provide increased handling properties, may have irrigation resistance, and/or may support cellular penetration. Flexibility of the covering may be selected to suit particular applications. In some applications, it may be desirable to have a flexible covering.

If the covering is made from a resorbable material, the covering degrades and disappears after a period of time. If the covering is not made of a resorbable material, the covering remains in the body. Tissue ingrowth may occur to bind the host tissue to the substance provided within the covering. Tissue ingrowth through and around the covering, between the host tissue and the substance provided within the covering, may be promoted via openings in the covering.

In various embodiments, the covering may comprise a porous material or a mesh material. The size of the pores of the covering may be designed to permit cellular infiltration (approximately several microns to several millimeters), but may also be designed specifically to exclude cells for the inside of the covering (e.g. approximately 0.45 microns) and only allow diffusion of small molecules (proteins and hormones). Thus, the covering may act to control access to the interior of the delivery system by cells. In embodiments comprising more than one compartment, characteristics of the covering material may be varied between compartments. Generally, the porosity, flexibility, strength, or any other characteristic of one compartment may vary from that characteristic of the other compartment.

The covering may be formed of a resorbable or nonresorbable, natural or synthetic biocompatible material. In some embodiments, more than one material may be used, including as multiple layers. For example, in an embodiment comprising two compartments, one or more materials may be used for the first compartment and a different material or materials may be used for the second compartment. For example, one compartment or portions thereof may be made of material or materials that provide a desired property or properties relative to other compartments or portions thereof, such as increased or decreased resorbability or stiffness, or the different compartments or portions thereof may be imparted with different drug delivery properties, etc. Alternatively, all compartments may comprise the same material or mixtures of materials. Where the characteristics of the material are varied between compartments, or over the surface of a single compartment, the pores of the first compartment or portion thereof may be larger than the pores of the second compartment.

The covering may comprise any suitable structure for delivering a substance in vivo. Thus, as described, the covering may comprise a mesh. In other embodiments, the covering may comprise a polymeric structure with a chamber provided therein. The chamber may be filled with a substance for delivering in vivo, such as autograft, demineralized bone matrix, or others disclosed herein.

In some embodiments, the covering may expand when placed in the body. Expansion can be provided in at least two ways: the covering may be compressed such that the covering expands when placed in the body or the covering may be made of a material that expands when it comes in contact with water or other bodily fluids, either by way of liquid absorption, or by stretching when the materials inside it absorb liquid and themselves expand. In some embodiments, the covering may comprise a shape memory material such as copper-zinc-aluminum-nickel alloy, copper-aluminum-nickel alloy, or nickel-titanium (NiTi) alloy. Reinforcing materials such as cortical bone, calcium phosphates, may also be incorporated into the structure of the covering to reinforce it.

The covering may be configured for specific compressive strength and rigidity by adjusting density and resorption time of the covering. In some embodiments, a coating may be provided over the covering. For example, the coating may be a compound of poly-L-lactide, of polyglycolic acid, or their polymers. The coating may be selected such that it has a resorption time wherein it is resorbed by the body and the material within the covering is permitted to exit through openings in the covering.

A covering according to an aspect of the present application may comprise at least one of bioerodible polymers, bioabsorbable polymers, biodegradable biopolymers, synthetic polymers, copolymers and copolymer blends or combinations thereof. Exemplary materials may include biopolymers and synthetic polymers such as human skin, human hair, bone sheets, collagen, fat, thin cross-linked sheets containing fibers and/or fibers and chips, degradable sheets made from polyethylene glycol (PEG), chitosan sheets, alginate sheets, cellulose sheets, hyaluronic acid sheet, as well as copolymer blends of poly (lactide-co-glycolide) PLGA.

Advantageously, a covering according to an aspect of the present application utilizes polymer materials, which provide increased shelf life and further impart and/or improve moisture and/or radiation resistance. Accordingly, a covering provides improved stability, is resistant to environmental degradation, and provides increased durability to e.g., sterilization procedures.

Exemplary materials may include polymeric material (for example, see U.S. Pat. Nos. 6,696,073, 6,478,825, 6,440,444, and 6,294,187 and U.S. Patent Publications Nos. 2006/0216323 and 2005/0251267, all herein incorporated by reference in their entirety); woven material and braided material (for example, see U.S. Patent Publication No. 2005/0283255, herein incorporated by reference in its entirety); non-woven; shape memory material; using outer particles to contain inner particles; attach particles to threads; add porosity to mesh fibers; non-porous materials; non-porous materials. In some embodiments, materials may be used for portions of the covering, such as for a compartment of the covering, which may be substantially impenetrable.

In some embodiments, the covering may comprise a mesh material. Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly (glycolic acid) (PGA), poly(lactic acid-glycolic acid) (PLGA), polydioxanone, PVA, polyurethanes, polycarbonates, and others. Other suitable materials include carbon fiber, metal fiber, and various meshes. In other embodiments, the covering may comprise non-woven material such as spun cocoon or shape memory materials having a coil shape or shape memory alloys.

Generally, the covering may be formed of any natural or synthetic structure (tissue, protein, carbohydrate) that can be used to form a covering configuration. Thus, the covering may be formed of a polymer (such as polyalkylenes (e.g., polyethylenes, polypropylenes, etc.), polyamides, polyesters, poly(glaxanone), poly(orthoesters), poly(pyrolicacid), poly (phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite, etc.), PEEK (polyether-etherketone), dessicated biodegradable material, metal, composite materials, a biocompatible textile (e.g., cotton, silk, linen), extracellular matrix components, tissues, or composites of synthetic and natural materials, or other. Various collagen materials can be used, alone or in combination with other materials, including collagen sutures and threads. Any suitable collagen material may be used, including known collagen materials, or collagen materials as disclosed in U.S. patent application Ser. No. 12/030,181, filed Feb. 12, 2008, hereby incorporated by reference in its entirety, which discloses collagen materials that may be used for forming a covering. Some examples include polymer or collagen threads woven, or knitted into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds.

In some embodiments, mesh fibers may be treated to impart porosity to the fibers. This may be done, for example, to PLA, PLGA, PGA, and other fibers. One suitable method for treating the mesh fibers comprises supercritical carbon dioxide treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated such as by having particles adhered thereto. The particles may be, for example, bone particles. Thus, in one embodiment, the covering may comprise a plurality of threads formed into a fabric. The threads may have particles adhered thereto. For example, the threads may have particles strung on the thread. In an alternative embodiment, the covering may be formed of a material and the material may be coated with particles.

In yet other embodiments, the covering may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery system for delayed delivery of cells, growth factors, or bone morphogenetic proteins is provided comprising a non-porous covering.

In particular, in various embodiments, the device may comprise a bioerodible, a bioabsorbable, and/or a biodegradable biopolymer that may provide immediate release, or sustained release of the clonidine. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly (orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG and/or PEG may be used as a plasticizer for PLGA, but other polymers/ excipients may be used to achieve the same effect. mPEG imparts malleability to the resulting formulations. In some embodiments, these biopolymers may also be coated on the medical device to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the medical device. In some embodiments, the range of the coating on the medical device ranges from about 5 microns to about 250 microns or 5 microns to about 200 microns to delay release from the medical device.

In various embodiments, the medical device comprises poly(lactide-co-glycolide) (PLGA), polylactide (PLA), polyglycolide (PGA), D-lactide, D,L-lactide, L-lactide, D,L-lactide-co-ϵ-caprolactone, D,L-lactide-co-glycolide-co-ϵ-caprolactone, L-lactide-co-ϵ-caprolactone or a combination thereof.

The covering material may have functional characteristics. Alternatively, other materials having functional characteristics may be incorporated into the covering. Functional characteristics may include radiopacity, bacteriocidity, source for released materials, tackiness, etc. Such characteristics may be imparted substantially throughout the covering or at only certain positions or portions of the covering.

Suitable radiopaque materials include, for example, ceramics, mineralized bone, ceramics/calcium phosphates/ calcium sulfates, metal particles, fibers, and iodinated polymer. Polymeric materials may be used to form the covering and be made radiopaque by iodinating them. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

Functional material, such as radiopaque markers, may be provided at one or more locations on the covering or may be provided substantially throughout the covering. Thus, for example, in a tubular covering, a radiopaque marker may be provided at a tip of the tubular covering. Such marker may facilitate placement of the covering. Radiopaque materials may be incorporated into the covering and/or into the substance for delivery by the covering. Further, radiopaque materials may be provided at only some locations on the covering such that visualization of those locations provides indication of the orientation of the covering in vivo.

The covering itself may be designed to release materials during degradation of the covering material. Thus, bone morphogenic proteins (BMPs), growth factors, antibiotics, angiogenesis promoting materials (discussed more fully below), bioactive agents (discussed more fully below), or other actively releasing materials may be incorporated into the covering material such that as the covering material is degraded in the body, the actively releasing material is released. For example, an actively releasing material may be incorporated into a biodegradable polymer covering such as one manufactured of a biodegradable polyester such as poly (lactic acid) (PLA), poly(glycolic acid) (PGA), poly(lactic-co-glycolic acid) (PLGA), or polyhydroxyalkanoates (polyhydroxybutyrates and polyhydroxyvalerates and copolymers). In some embodiments, poly(ethylene glycol) (PEG) may be incorporated into the biodegradable polyester to add hydrophilic and other physico-chemical properties to enhance drug delivery. In some embodiments, composites of allograft bone and biodegradable polymers (for example, PLEXUR® products available from Osteotech) may be used in the covering.

In some embodiments, the covering may comprise a material that becomes tacky upon wetting. Such material may be, for example, a protein or gelatin based material. Tissue adhesives, including mussel adhesive proteins and cryanocrylates, may be used to impart tackiness to the covering. In further examples, alginate or chitosan material may be used to impart tackiness to the covering. In further embodiments, an adhesive substance or material may be placed on a portion of the covering or in a particular region of the covering to anchor that portion or region of the covering in place at an implant site.

In one embodiment there is a covering comprising two compartments, where first and second materials may be used for the first and second compartments, respectively. The first material may release or expose a growth factor according to a first rate and the second material may release a growth factor according to a second rate. Further, the growth factors released by the first and second compartments may be the same or may be different. For example, an angiogenic growth factor may be provided with the first compartment and an osteoinductive growth factor may be provided with the second compartment.

Covering Configurations

The shape, configuration, or form of the covering may be selected for particular applications. Such shape and configuration may include, for example, the basic shape of the covering (e.g., a cylinder, a bag, or a pouch, etc.), whether the covering has a single or a plurality of compartments, and whether the covering includes attachment mechanisms. The covering (or delivery system) may be configured to conform to surrounding bony contours of the space in which it is placed.

As previously discussed, the covering may be formed of as a mesh. Thus, the covering may comprise a woven material. The woven material may have varying degrees of permeability. It may be permeable, semi-permeable, or non-permeable. Permeability may be with respect to cells, to liquids, to proteins, to growth factors, to bone morphogenetic proteins, or other. In further embodiments, the material may be braided.

In alternative embodiments, the covering may comprise a substantially solid structure, such as a polymer structure with a chamber, or a spun cocoon.

The covering may have any suitable configuration. For example, the covering may be formed as a ring, a cylinder, a cage, a rectangular shape, a mesh, a suture-like wrap, a continuous tube, or other configuration. In specific embodiments, the covering may be formed as a thin tube designed to be inserted through catheters or an introducer tube, a rectangular shape designed to fit adjacent to spinal processes for posterolateral spine fusion, a cube like structure designed to fit between vertebral bodies or within cages for interbody spinal fusion, a tube-like shape where the ends are designed to be fitted onto nonunion long bone defects, relatively flat shapes designed to fill cranial or maxillofacial defects, rectangular structures designed for osteochondral defects, structures preshaped to fit around various implants (e.g. dental, doughnut with hole for dental implants), or relatively elastic ring-like structures that will stretch and then conform to shapes (e.g. rubber band fitted around processes). In an embodiment wherein the covering is formed as a cage, the cage may comprise a plurality of crossed filaments which define between them a series of openings for tissue ingrowth. Any of these shapes may be used for a covering comprising a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The configuration of the covering may be determined by the substance to be provided within the covering. For example, if the substance to be contained comprises fibers, the covering may be formed as strings or sutures that are wrapped around the fibers.

In certain embodiments, a bone void can be filled. A compartment within the covering material can be at least partially filled with a bone repair substance. In various embodiments, at least partially filled as used herein, can mean that a percentage of the volume of a compartment (or covering material, as applicable) is at least 70% occupied, at least 75% occupied, at least 80% occupied, at least 85% occupied, at least 90% occupied, at least 95% occupied, or 100% occupied. The covering material can be inserted into an opening in the defect until the defect is substantially filled. In various embodiments, a substantially filled as used herein can mean that a percentage of the volume of a defect (or covering material, as applicable) is at least 70% occupied, at least 75% occupied, at least 80% occupied, at least 85% occupied, at least 90% occupied, at least 95% occupied, or 100% occupied. The excess material extending beyond the surface of the bone if the bone were without the defect can then be removed, or at least partially removed such that the opening of the defect is flush with the uninjured bone surface.

A covering as provided herein may further comprise an attachment or coupling mechanism. Any suitable attachment mechanism can be used, such as a tab, loop, tack or other structure adapted for attachment at the site. Also, for example, a covering may include a hook-and-eye (Velcro™) portion. The hook-and-eye portion may be used to couple the covering to a tissue structure, such as bone, or to another covering. For example, a dual compartment covering may be formed by two single-compartment coverings coupled at complementary ends thereof. For example, the coupling portion may comprise overlapping/mating Velcro™ portions. The size and shapes of the single compartment coverings may be the same or may be different. Further, the materials of the compartment coverings and the substances provided therein may be the same or may be different. The coupling may be done pre-implantation or post-implantation. In post-implantation embodiments, the coupling may be done by inserting first and second coverings through an opening into a space and coupling the coverings within the space. Other suitable attachment, or coupling, mechanisms are described more fully below.

In some embodiments, the covering may be labeled. Such labeling may be done in any suitable manner and at any suitable location on the covering. In some embodiments, labeling may be done by using a silk screen printing, using an altered weaving or knotting pattern, by using different colored threads, or other. The labeling may indicate information regarding the covering. Such information might include part number, donor id number, number, lettering or wording indicating order of use in the procedure or implant size.

Bioactive Agents

A substance is provided inside the covering, before or during surgery (as described below), for delivery in vivo. Generally, the substance or material may be homogenous or heterogeneous. The substance or material may be selected to exhibit certain gradients. For example, the substance or material may be selected to exhibit a gradient to guide, lure, or attract cells along a pathway. Such gradient may comprise a cell gradient, a cell type gradient (for example transitioning from bone cells to cartilage cells or transitioning from bone cells to tendon cells), a gradient of conductivity, or a gradient of density/porosity. In some embodiments, the substance or material may comprise a sequence of ingredients.

The covering may be used to deliver a substance comprising any suitable biocompatible material. In specific embodiments, the covering may be used to deliver surface demineralized bone chips, optionally of a predetermined particle size, demineralized bone fibers, optionally pressed, and/or allograft. For embodiments wherein the substance is biologic, the substance may be autogenic, allogenic, xenogenic, or transgenic. Other suitable materials that may be positioned in the covering include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In some embodiments, the substance may be pressed before placement in the covering. A substance provided within the covering may be homogenous, or generally a single substance, or may be heterogeneous, or a mixture of substances.

In some embodiments, the covering can comprise one or more compartments having demineralized bone material therein. The demineralized bone material can be comprise demineralized bone, powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. In some embodiments, the covering may comprise some fully mineralized bone material. The configuration of the bone material can be obtained by milling, shaving, cutting or machining whole bone as described in for example U.S. Pat. No. 5,899,939. The entire disclosure is herein incorporated by reference into the present disclosure.

In some embodiments, the covering comprises elongated demineralized bone fibers having an average length to average thickness ratio or aspect ratio of the fibers from about 50:1 to about 1000:1. In overall appearance the elongated demineralized bone fibers can be in the form of threads, narrow strips, or thin sheets. The elongated demineralized bone fibers can be substantially linear in appearance or they can be coiled to resemble springs. In some embodiments, the elongated demineralized bone fibers are of irregular shapes including, for example, linear, serpentine or curved shapes. The elongated bone fibers can be demineralized however some of the original mineral content may be retained when desirable for a particular embodiment.

In some embodiments, the covering comprises elongated demineralized bone fibers and chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the bone material that can be filled in the covering can comprise a combination of fully mineralized bone material (e.g., fiber, chips, particles, etc.) and demineralized bone material (e.g., fiber, chips, particles, etc.).

In some embodiments, the biocompatible material comprises demineralized bone matrix fibers and demineralized bone matrix chips in a 30:60 ratio.

In some embodiments, the demineralized bone material can be in the covering and comprises from about 1 to about 70 micrometers particle size range or from about 125 to about 250 micrometer particle size range.

In some embodiments, the covering may have a modulus of elasticity in the range of about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$. After the cover is administered to the target site, the covering may have a modulus of elasticity in the range of about $1\times-10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In some embodiments, the substance may be designed to expand in vivo. Such an embodiment may be used to fill a space and create contact with congruent surfaces as it expands in vivo, for example for interbody fusion. Thus, in some embodiments, the delivery system may be used in the disc space, between implants, or inside a cage.

The covering retains the substance in place by pressure against the covering. The covering thus may, in some embodiments, maintain particles of substance in close proximity (for example, where the covering retains a substance comprising bone particles). Generally, the ratio of covering material to substance for placement within the covering may be low. For example, in some embodiments, the ratio of covering material to substance, by weight, may be approximately 1:1,000, 1:100, 1:50, 1:25, 1:1, or any suitable ratio that may be higher or lower than these.

In some embodiments the substance delivered by the covering may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In one embodiment of a covering comprising two compartments, a first growth factor may be provided for delivery by the first compartment and a second growth factor may be provided for delivery by the second compartment. The first and second growth factors may be provided with other substances. The first and second growth factors may be selected (and placed in respective compartment for positioning in vivo) based on desired characteristics of the growth factor. For example, an angiogenic growth factor may be provided in the first compartment and an osteoinductive growth factor may be provided in the second compartment.

Similarly, the substance delivered by the first compartment and the substance delivered by the second compartment may be selected based on desired characteristics of the compartment according to its placement in vivo. Thus, for example, one compartment may have a substance that is substantially osteoclast stimulating while another compartment may have a substance that is substantially osteoblast stimulating.

In one embodiment, demineralized bone fibers may be provided in the first compartment and surface demineralized bone chips may be provided in the second compartment. In this embodiment, the demineralized bone fibers may generally provide osteoinductive characteristics and the surface demineralized chips may generally provide osteoinductive and/or osteoconductive characteristics. In use, the covering may be laid flat on the transverse process and positioned such that the first compartment, holding the demineralized bone fibers, is nearest the vertebral body and the second compartment, holding the surface demineralized bone chips, is farther from the vertebral body, or the compartments may be positioned in any other desired configuration. In another embodiment, a covering may comprise first and second compartments wherein autograft may be placed in one of the compartments prior to placement of the covering in vivo, described more fully below. In other embodiments, three or more compartments may be used, as appropriate for the materials being delivered and the application of the compartmented implant. More than one substance may be provided in a compartment. For example, surface demineralized bone chips and demineralized bone fibers may be mixed and provided within a single compartment. Such mixture of substances within a single compartment may be a substantially uniform mix or may be a plurality of substances placed in the compartment separately such that they are substantially unmixed. When multiple compartments are used, each compartment may contain one or more substances. Exemplary substances that may be provided in one or more compartments of the delivery system include cells from the osteogenic precursors, growth factors, angiogenic factors and other active proteins including bone morphogenic proteins, and cellular scaffolding materials of natural or synthetic origin, antibiotics, and other substances described below.

In some embodiments, other medical devices may be provided within the covering. For example, one or more electrical stimulator electrodes may be provided within the covering.

Kit of the Filling System

Figure 12:
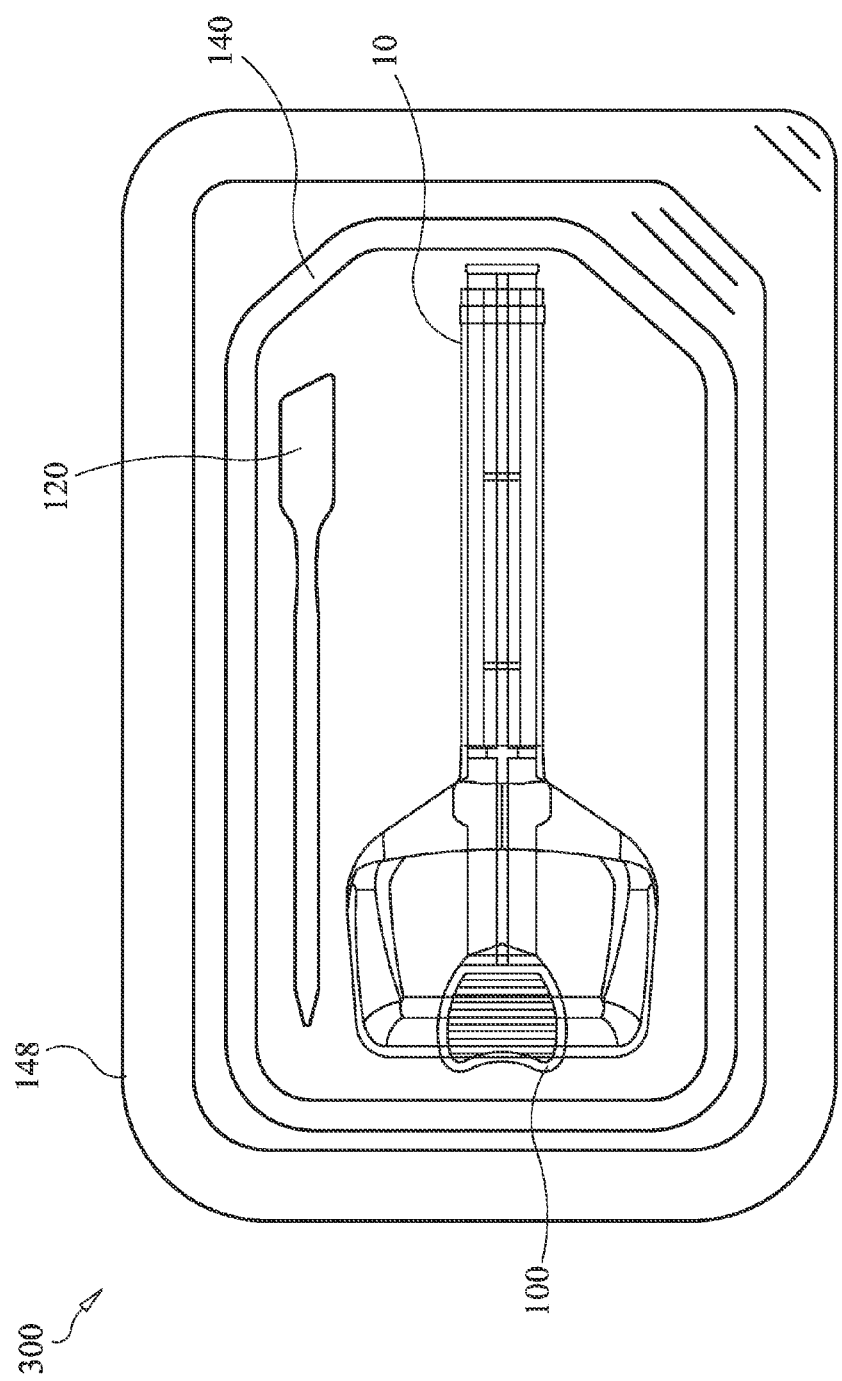
FIG. 12 depicts a kit according to an aspect of the present application.
Figure 13:
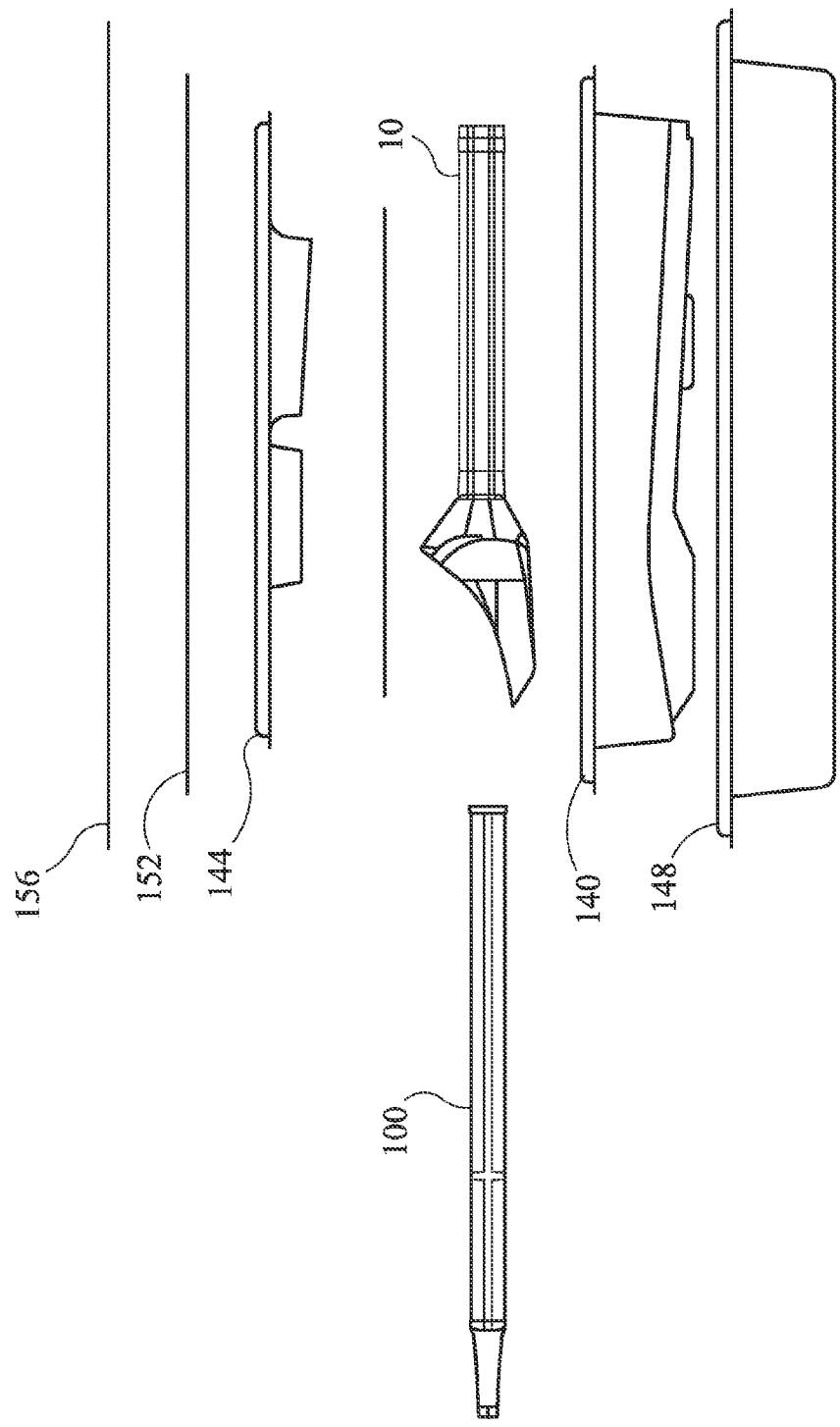
FIG. 13 is an exploded side view of several elements of the kit illustrated in FIG. 12.
Figure 14:
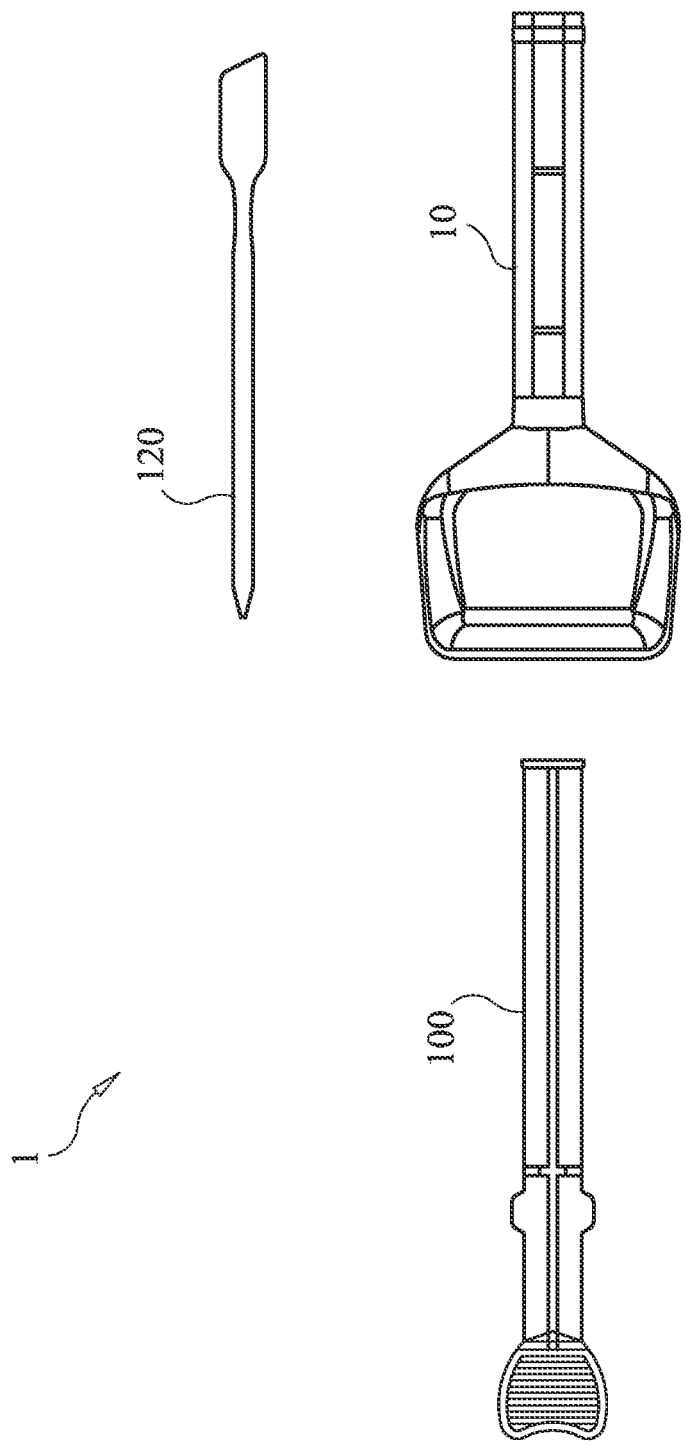
FIG. 14 is an exploded view of a funnel shaped container, a plunger and a spatula of the kit illustrated in FIG. 12.

FIGS. 12, 13 and 14 show devices of the filling system 1, arranged as a kit 300, which are usable to deliver bone graft material into a bone bag. The number and type of devices can vary. FIG. 12 shows eight representative devices, each having a different size and function. In various embodiments, the devices included in kit 300 are at least sterilized, made of plastic, transparent or translucent material: funnel shaped container 10; plunger 100; spatula 120; inner tray 140 with recesses configured to receive devices 10, 100 and 120; retainer 144 that can hold all kit devices together in place; outer tray 148 which contains all elements; inner lid 152 and outer lid 156 can seal all kit elements from the environment. Referring to FIG. 14, devices 140, 144, 148, 152 and 156 have been removed from this view again, for additional clarity.

Sterilization

The filling system including at least the funnel shaped container 10, plunger 100, spatula 120 as well as the covering device 200 may be sterilizable. In various embodiments, one or more components of the filling system and/or covering are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device and/or covering. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device and/or covering. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the medical device and/or covering are included in a gel.

Other methods may also be used to sterilize the device and/or covering and/or one or more components of the device and/or covering, including, but not limited to, gas sterilization, such as, for example, with ethylene oxide or steam sterilization.

Methods of Use

A method of filling a covering utilizing the filling system described herein is also provided. In various embodiments, the method of filling the covering with at least one substance comprises providing a covering having at least one flared opening; providing a funnel shaped container having a scoop portion connected to a hollow barrel, the barrel configured for insertion into the flared opening of the cover; providing at least one substance into the funnel shaped container; providing a plunger having an elongated portion and a flared handle, and pushing the at least one substance with the plunger through the barrel into the covering. In some embodiments, a spatula can be used to provide the at least one substance into the covering.

In some aspects, the at least one substance comprises autograft, allograft, demineralized bone matrix fiber, demineralized bone chips or a combination thereof. In various embodiments, the method of filling a covering can further comprise adding a bioactive material to the at least one substance. In certain aspects, the bioactive material comprises protein, bone morphogenetic proteins, carbohydrate, lipids, collagen, allograft bone, autograft bone, tricalcium phosphate, hydroxyapatite, growth and differentiation factors, carriers for growth factors, growth factors extracts of tissue, bone marrow aspirate, concentrates of lipid derived or marrow derived adult stem cells, umbilical cord derived stem cells, committed or partially committed cells from osteogenic or chondrogenic lineage, antimicrobials, antibiotics, statins, or combinations thereof.

Although the invention has been described with reference to preferred embodiments, persons skilled in the art will recognize that changes may be made in form and detail without departing from the spirit and scope of the invention.

What is claimed is:

1. A filling system for delivery of at least one substance to a covering, the filling system comprising the covering, a funnel shaped container and a plunger, the covering comprising a compartment, the funnel shaped container comprising a scoop portion connected to a hollow barrel, the scoop portion comprising a central flat base, the barrel configured for insertion into the covering, the barrel having a proximal opening configured to receive a portion of the plunger and a distal opening to dispense the at least one substance into the covering, the plunger adapted for slidingly pushing the at least one substance through the hollow barrel out of the distal opening and into the covering, the plunger comprising a smooth elongated portion extending within the hollow barrel, a projection and a flared solid handle at one end of the plunger, the projection and the solid flared handle being wider than an inner diameter of the hollow barrel so that the projection and the solid flared handle prevent the one end of the plunger from entering into the hollow barrel.

2. A filling system according to claim 1, wherein the central flat base is connected to a front wall, opposite side walls and a funnel shaped neck opposite the front wall.

3. A filling system according to claim 1, wherein the hollow barrel has a top end and a bottom end, the top end connected to a funnel shaped neck and the bottom end comprising a bulge configured for insertion into the covering.

4. A filling system according to claim 2, wherein the funnel shaped neck forms an axial access channel at one end adjoining the central flat base and at the opposite end defines an opening connecting the neck to the barrel.

5. A filling system according to claim 1, wherein the elongated portion extends the length of the barrel from a top end to a bottom end and is configured to slidingly access the hollow barrel.

6. A filling system according to claim 1, further comprising a spatula for dispensing the at least one substance for introduction into the funnel shaped container.

7. A filling system according to claim 6, wherein the spatula comprises a stalk portion having two ends, a conical tip at one end and a shovel area at the opposite end.

8. A filling system according to claim 3, wherein the covering has at least one compartment comprising an elongated containment having a first end and a second end opposite each other, the elongated containment defining an opening configured to receive the at least one substance, the elongated containment adapted to receive a closing member.

9. A filling system according to claim 8, wherein the opening of the covering is flared and configured to receive a bulge of the barrel.

10. A filling system according to claim 8, wherein the closing member comprises drawing strings, stitches, sutures, wing sutures, heat seals, adhesion, pressure fittings, coil ring, twist ties or combinations thereof.

11. A filling system according to claim 1, wherein the at least one substance comprises autograft, allograft, demineralized bone matrix fiber, demineralized bone chips or a combination thereof.

12. A filling system according to claim 2, wherein the funnel shaped neck further comprises a first fluted portion and a second fluted portion, the first fluted portion and the second fluted portion are contiguous and comprise a top rim.

13. A kit facilitating the placement of at least one substance within a covering, the kit comprising: a funnel shaped container having a scoop portion connected to a barrel and a plunger, the barrel having a proximal opening configured to receive a portion of the plunger and a distal opening to dispense the at least one substance into the covering, the scoop portion comprising a central flat base, the plunger adapted to slide through the barrel of the funnel shaped container for pushing the at least one substance out of the distal opening and into the covering, the plunger comprising a smooth elongated portion extending within the hollow barrel, a projection and a flared solid handle at one end of the plunger, the projection and the solid flared handle being wider than an inner diameter of the hollow barrel so that the projection and the solid flared handle prevent the one end of the plunger from entering into the hollow barrel; an inner tray with recesses configured to receive the funnel shaped container and the plunger; a retainer positioned on top of the inner tray, the retainer for holding the funnel shaped container and plunger in place; an inner lid and an outer lid for sealing the funnel shaped container and the plunger from the environment.

14. A kit according to claim 13, further comprising a spatula, the spatula having a stalk portion and a truncated shovel end, the shovel adapted to pack the at least one substance into the funnel shaped container.

15. A method of filling a covering with at least one substance which comprises:
providing a covering having at least one flared opening;
providing a funnel shaped container having a scoop portion connected to a hollow barrel, the hollow barrel having a proximal opening configured to receive a portion of a plunger and a distal opening configured to dispense at least one substance into the covering, the scoop portion comprising a central flat base, the barrel configured for insertion into the flared opening of the cover;
providing the at least one substance into the funnel shaped container;
providing the plunger comprising a smooth elongated portion extending within the hollow barrel, a projection and a flared solid handle at one end of the plunger, the projection and the solid flared handle being wider than an inner diameter of the hollow barrel, and pushing the at least one substance with the plunger through the barrel out of the distal opening and into the covering.

16. A method according to claim 15, wherein a spatula provides the at least one substance into the covering.

17. A method according to claim 15, wherein the at least one substance comprises autograft, allograft, demineralized bone matrix fiber, demineralized bone chips or a combination thereof.

18. A method according to claim 15, further comprising adding a bioactive material to the at least one substance.

19. A method according to claim 18, wherein the bioactive material comprises protein, bone morphogenetic proteins, carbohydrate, lipids, collagen, allograft bone, autograft bone, tricalcium phosphate, hydroxyapatite, growth and differentiation factors, carriers for growth factors, growth factors extracts of tissue, bone marrow aspirate, concentrates of lipid derived or marrow derived adult stem cells, umbilical cord derived stem cells, committed or partially committed cells from osteogenic or chondrogenic lineage, antimicrobials, antibiotics, statins, or combinations thereof.

\* \* \* \* \*

UNITED STATES PATENT AND TRADEMARK OFFICE
CERTIFICATE OF CORRECTION

| | | |
|---|---|---|
| PATENT NO. | : 9,283,013 B2 | Page 1 of 1 |
| APPLICATION NO. | : 13/829416 | |
| DATED | : March 15, 2016 | |
| INVENTOR(S) | : Shimko et al. | |

It is certified that error appears in the above-identified patent and that said Letters Patent is hereby corrected as shown below:

Specification

In Column 13, Line 31, delete "(PGA)," and insert -- (PG), --, therefor.

In Column 13, Lines 64-65, delete "morphogenic" and insert -- morphogenetic --, therefor.

In Column 18, Line 43, delete "morphogenic" and insert -- morphogenetic --, therefor.

In Column 18, Line 53, delete "(PDLGF);" and insert -- (PDGF); --, therefor.

In Column 19, Line 50, delete "morphogenic" and insert -- morphogenetic --, therefor.

Signed and Sealed this
Fourteenth Day of June, 2016

Michelle K. Lee
*Director of the United States Patent and Trademark Office*